(12) United States Patent
Abraham

(10) Patent No.: US 7,148,210 B2
(45) Date of Patent: Dec. 12, 2006

(54) METHOD OF TREATING BONE METASTASIS

(75) Inventor: Edward H. Abraham, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 206 days.

(21) Appl. No.: 10/687,102

(22) Filed: Oct. 15, 2003

(65) Prior Publication Data

US 2004/0116375 A1    Jun. 17, 2004

Related U.S. Application Data

(60) Provisional application No. 60/418,797, filed on Oct. 15, 2002.

(51) Int. Cl.
    *A61K 31/675* (2006.01)
(52) U.S. Cl. .............................. 514/79; 514/81; 514/82
(58) Field of Classification Search .................. 514/80, 514/79, 81, 82
    See application file for complete search history.

(56) References Cited

U.S. PATENT DOCUMENTS

| 4,291,024 | A  |   | 9/1981 | Turcotte ..................... 424/180 |
| 4,880,918 | A  |   | 11/1989 | Rapaport ..................... 536/27 |
| 5,049,372 | A  | * | 9/1991 | Rapaport ..................... 424/1.77 |
| 5,641,500 | A  |   | 6/1997 | Trepel et al. ............... 424/422 |
| 2003/0004140 | A1 | * | 1/2003 | Dalton et al. ............... 514/102 |
| 2005/0130922 | A1 | * | 6/2005 | Altaba et al. .................. 514/44 |

OTHER PUBLICATIONS

Bolger et al., "Strontium-89 (Metastron) Versus External Beam Radiotherapy in Patients With Painful Bone Metastases Secondary to Prostatic Cancer:Preliminary Report of a Multicenter Trial", Seminars in Oncology 1993 20 (3) (Supplemental 2) :32-33.
Elomaa et al., "Disphosphonates for Osteolytic Metastases", Lancet 1985 vol. 1 (8438) :1155-1156.
Fishman et al., "Adenosine and Other Low Molecular Weight Factors Released by Muscle Cells Inhibit Tumor Cell Growth[1]", Cancer Research 1998 58:3181-3187.
Estrela et al., "Elimination of Ehrlich tumours by ATP-induced growth inhibition, glutathione depletion and X-rays", Nature Medicine 1995 1(1):84-88.
Fang et al., "$P_2$-Purinergic Receptor Agonists Inhibit the Growth of Androgen-independent Prostate Carcinoma Cells", J. Clin. Invest. 1992 89:191-196.
Galmarini et al., "Nucleotide analogues and nucleobases in cancer treatment", Lancet Oncol. 2002 3:415-424.
Janssens and Boeynaems, "Effects of extracellular nucleotides and nucleosides on prostate carcinoma cells", Br. J. Pharmacol. 2001 132:536-546.
Maymon et al., "Enhancing effect of ATP on intracellular adriamycin penetration in human ovarian cancer cell lines", Biochimica et Biophysica Acta 1994 1201:173-178.
Mure et al., "Modulation of Membrane Permeability, Cell Proliferation and Cytotoxicity of Antitumor Agents by External ATP in Mouse Tumor Cells", Jpn J. Cancer Res. 1992 83:121-126.
Rapaport et al., "Growth Inhibition of Human Tumor Cells in Soft-Agar Cultures by Treatment with Low Levels of Adenosine 5'-Triphosphate", Cancer Research 1983 43:4402-4406.
Rapaport Eliezer, "Treatment of Human Tumor Cells With ADP or ATP Yields Arrest of Growth in the S Phase of the Cell Cycle", J. Cell Physiol. 1982 114(3) :279-283.
Robinson Ralph G., M.D., "Strontium-89-Precursor Targeted Therapy for Pain Relief of Blastic Metastatic Disease", Cancer 1993 72:3433-3435.
Schroder and Rapaport, "Retinoic Acid Alters Subcellular Compartmentalization of ATP Pools in 3T3 Cells but Not in HeLa Cells", J. Cell Physiol. 1984 120(2) :204-210.
van Holten-Verzantvoort et al., "Reduced Morbidity from Skeletal Metastases in Breast Cancer Patients During Long-Term Bisphosphonate (APD) Treatment", Lancet 1987 2(8566) 983-.
von Albertini et al., "Extracellular ATP and ADP Activate Transcription Factor NF-$_K$B and Induce Endothelial Cell Apoptosis", Biochem. Biophys. Res. Commun. 1998 248 (3) :822-829.
von Albertini et al., "Adenosine Nucleotides Induce E-Selectin Expression in Porcine Endothelial Cells", Transplant Proc. 1997 29(1-2) :1062.

* cited by examiner

*Primary Examiner*—Alton Pryor
(74) *Attorney, Agent, or Firm*—Licata & Tyrrell P.C.

(57) ABSTRACT

The invention provides a drug combination for the treatment of diseases associated with bone metastasis. The combination provides adenosine or a derivative thereof, a bisphosphonate, and a targeting agent(s) to decrease the signs or symptoms associated with such diseases.

2 Claims, No Drawings

METHOD OF TREATING BONE METASTASIS

This application claims the benefit of priority from U.S. provisional application Ser. No. 60/418,797, filed on Oct. 15, 2002, whose contents is incorporated herein by reference in its entireties.

BACKGROUND OF THE INVENTION

Bone metastases are a common cause of morbidity in cancer patients. The debilitating pain that occurs in many patients with advanced malignancies is primarily produced by bone metastases. Spinal metastases can produce cord compression and severe neurologic impairment. Many malignancies can result in bone metastases including breast cancer (median survival time is 20 to 30 months), lung cancer (median survival of less than 6 months), and prostate cancer (the second leading cause of cancer deaths in men in the United States) account for more than 80% of bone metastases. Conversely, more than 50% of patients with these primary cancers will eventually develop bone metastases (Malawer and Delaney In: DeVita, et al., eds. Cancer: Principles and Practice of Oncology. Philadelphia: JB Lippincott Company, 4$^{th}$ Edition, 1993, pp 2225–2245).

The management of bone metastases depends on a number of factors: the location and extent of bony destruction, the severity of morbidity, the availability of effective systemic therapies (hormonal or chemotherapy), and the overall status of the patient. Bisphosphonates have been shown to promote healing and lessen pain in patients with osteolytic metastases (van Holten-Verzantvoort, et al. (1987) *Lancet* 2(8566):983–985; Elomaa, et al. (1985) *Lancet* 1(8438): 1155–1156). Some hematologic malignancies that involve bone, particularly the lymphomas, may be cured with systemic hormonal therapy or radiotherapy, but for most patients with bone metastases, palliation is the goal of therapy. Radioisotopes such as strontium-89 and samarium-153 have been shown to decrease pain in patients with osteoblastic metastases resulting from prostate cancer (Robinson (1993) *Cancer* 72(Suppl.):3433–3435; Bolger, et al. (1993) *Seminars in Oncology* 20(Suppl. 2):32–33).

There is a need in the art for effective combined therapies capable of placing advanced stage widespread metastases into remission.

ATP has as physiological role in aging and tumor development. Lowered contents of adenine compounds in the erythrocytes and thrombocytes obtained from patients with various neoplastic malignancies has been observed (Laciak and Witkowski (1966) *Otolaryngol Pol.* 20(2):269–75; Wand and Rieche (1972) *Dtsch Gesundheitsw.* 27(23):1072–6; De la Morena Garcia, et al. (1977) *Rev. Clin. Esp.* 146(5):221–3; Stocchi, et al. (1987) *Tumori* 73(1): 25–8). Likewise, human blood ATP levels decline as individuals age (Rabini, et al. (1997) *Eur. J. Clin. Invest.* 27(4):327–32). Furthermore, there exists a relationship between aging and the development of cancer (Henson and Tarone (1994) *Cancer* 74(1 Suppl):424–9; Braendle (2000) *Ther. Umsch.* 57(10):646–50; Kikuchi, et al. (2000) *Jpn. J. Cancer Res.* 91(8):774–9; Cortopassi and Wang (1996) *Mech. Ageing Dev.* 91(3):211–8; Liu, et al. (1994) *Proc. Natl. Acad. Sci. USA* 91(19):8910–4).

The genetic disease Cystic Fibrosis (CF) is associated with elevated levels of blood ATP. Age-adjusted rates of prostate, breast and other tumors were shown to decrease in individuals homozygous for the CF defect and who had elevated blood ATP levels (Warren, et al. (1991) *BMJ* 302(6779):760–1; Padua, et al. (1997) *Hum. Mutat.* 10(1): 45–8; Neglia, et al. (1995) *N. Engl. J. Med.* 332(8):494–9; Abraham, et al. (1996) *Nat. Med.* 2(5):593–6; Miro and Orecchia (2002) *Lancet Oncol.* 3(7):395).

An inverse relationship exists between exercise and tumor development in experimental animals (Daneryd, et al. (1998) *Cancer Res.* 58(23):5374–9; Daneryd, et al. (1990) *Eur. J. Cancer* 26(10):1083–8; Daneryd, et al. (1995) *Eur. J. Cancer* 31A(13–14):2309–12; Fishman, et al. (1998) *Cancer Res.* 58(14):3181–7). In exercising rats, tumor volumes are significantly reduced in a manner inversely related to tumor ATP pools. Exercising human muscles release significant amounts of adenosine and ATP (Hellsten, et al. (1998) *Circulation* 98(1):6–8; Hellsten, et al. (1998) *Am. J. Physiol.* 274(4 Pt 1):E600–6). It was found that tumor metastases to striated muscle are clinically rare. The elevations in ATP and its catabolic products, ADP, AMP and adenosine were directly analyzed in the interstitium of exercising skeletal muscle and these elevations were directly related to the level of work performed by the muscle. A recent study concluded that low molecular weight factors, which are released by muscle cells and are inhibitory to tumor development and growth, were adenosine and its related compounds (Fishman, et al. (1998) *Cancer Res.* 58(14):3181–7). Therefore, extracellular purine levels are important in modulating tumor growth.

The significant depletion of host visceral energy stores by a growing tumor has been demonstrated in experimental animals (Inculet, et al. (1987) *J. Natl. Cancer Inst.* 79(5): 1039–46; Peacock, et al. (1987) *Surgery* 102(3):465–72; Schneeberger, et al. (1989) *Cancer Res.* 49(5):1160–4). Along with the decline in hepatic ATP pools in cachexia tumor animal models, severe declines in skeletal muscle ATP pools were demonstrated (Inculet, et al. (1987) *J. Natl. Cancer Inst.* 79(5):1039–46; Peacock, et al. (1987) *Surgery* 102(3):465–72; Schneeberger, et al. (1989) *Cancer Res.* 49(5):1160–4; Daneryd, et al. (1998) *Cancer Res.* 58(23): 5374–9; Daneryd, et al. (1995) *Eur. J. Cancer* 31A(13–14): 2309–12).

Relatively low levels of extracellular ATP inhibit the growth of a variety of human tumor cells and subsequently yield substantial cell killing in in vitro systems (Rapaport, et al. (1983) *Cancer Res.* 43(9):4402–6). The mechanism of tumor cell killing is attributed to the permeation of tumor cell membranes by extracellular ATP and the arrest the tumor cells in S-phase followed by cell death (Schroder and Rapaport (1984) *J. Cell Physiol.* 120(2):204–10; Rapaport, et al. (1983) *J. Cell Physiol.* 114(3):279–83). Nucleoside analogues and derivatives thereof are anti-tumor agents (U.S. Pat. Nos. 4,291,024; 4,880,918; and 5,641,500; Galmarini, et al. (2002) *Lancet Oncol.* 3:415–424; Janssens and Boeynaems (2001) *Br. J. Pharmacol.* 132:536; Fang, et al. (1992) *J. Clin. Invest.* 89:191). Radiolabeled adenine nucleotides also arrest the growth of tumor cells (U.S. Pat. Nos. 5,049,372). ATP- and diethylmaleate (DEM)-treated mice receiving a single dose of irradiation exhibit a reduction in viable cancer cells (Estrela, et al. (1995) *Nature Medicine* 1:84–88). However, without the thiol-depleting agent (DEM) radiation alone is not enough to eliminate cancer cells in tumor-bearing mice treated with ATP. Furthermore, ATP-induced glutathione depletion in combination with recombinant human tumor necrosis factor (rhTNF-α) results in a 61% inhibition of tumor growth (Obrador, et al. (1997) *Biochem. J.* 325:183–189).

In addition to its inherent cytolytic activities, extracellular ATP enhances the penetration of chemotherapeutic agents such as doxorubicin (Maymon, et al. (1994) *Biochim. Bio-* phys. Acta 1201(2):173–8) or vincristine (Mure, et al. (1992) *Jpn. J. Cancer Res.* 83(1):121–6) into tumor cells, significantly enhancing cell killing.

Extracellular ATP is a potent trigger of cell killing not only for tumor cells but also of associated endothelial cells that comprise the tumor vasculature. Extracellular ATP activates the transcription factor NF-kappa B through activation of the P2Z receptors. The ATP-induced generation of NF-kappa B leads to endothelial cell apoptotic death (von Albertini, et al. (1998) *Biochem. Biophys. Res. Commun.* 248(3):822–9; von Albertini, et al. (1997 *Transplant Proc.* 29(1–2):1062). Furthermore, U.S. Pat. No. 6,436,411 discloses the use of ATP to activate monocytes or macrophages to induce those cells to produce a number of immune stimulatory molecules including cytokines which may be used to treat cancer.

SUMMARY OF THE INVENTION

The present invention relates to a method of treating individuals with diseases associated with bone metastasis. The method involves administering an adenosine or derivative thereof in combination with a bisphosphonate and a targeting agent(s) to decrease the signs or symptoms of diseases associated with bone metastasis. In a preferred embodiment of the invention, the method of the invention further encompasses admininistering an agent which blocks adenosine receptors.

These and other aspects of the present invention are set forth in more detail in the following description of the invention.

agent(s). The disclosure provided herein is an example of the effectiveness of the drug combination and should not be construed as a limitation of the invention.

Treatment of hormone-refractory prostate adenocarcinoma (HRPA) patients presents a complex combination of tumor and pain management. Prostate-specific antigen (PSA) responses to various samarium-153 (sm-153) treatments, alone or in various combinations with total androgen suppression (TAS), ATP, and pamidronate (Pam, bisphosphonate) therapy are provided. HRPA outcomes and PSA measurements were determined pre- and post-treatment within 25–45 days after Sm-153 administration. PSA decreases were expressed as a negative value f % (Equation 1), hence, the larger the decrease the more negative the f %.

$$f\ \% = -\frac{(PSA\ \text{before}\ Sm\text{-}153 - PSA\ \text{after}\ Sm\text{-}153)}{PSA\ \text{before}\ Sm\text{-}153} \times 100 \qquad (\text{eq 1})$$

PSA decreases of greater than 50% from baseline are associated with improved survivals in prostate cancer patients [Zyskowski, et al. (2001) *Australas Radiol.* 45:39; Kelly, et al. (1993) *J. Clin. Oncol.* 11:607).

The effectiveness of the combination therapies provided herein demonstrated that Sm-153 (n=7)<TAS/Sm-153 (n=7) <pamidronate±TAS (n=13)<pamidronate/TAS/Sm-153 (n=4)<−5% PSA drop. Therefore, treating a patient having advanced prostate cancer with ATP followed by treatment with a bisphosphonate and sm-153 leads to a significant improvement in patient outcome. Furthermore, PSA levels significantly drop using this drug combination.

Infusional ATP has been generally well-tolerated in patents with advanced and metastatic cancer (Agteresch, et al (2000) *Eur. J. Clin. Pharmacol.* 56:49; Agteresch, et al. (2000) *Clin. Sci.* (Colch) 98:689; Agteresch, et al. (2000) *J. Natl. Cancer Inst.* 92:321; Agteresch, et al. (1999) *Drugs* 58:211) (Table 1).

TABLE 1

| Study | Avg Wt, kg | MTD, μg/kg/min | Duration, hours | Total ATP dose, gram | Daily ATP dose, gram | # of Infusions |
|---|---|---|---|---|---|---|
| 1 | 70.6 ± 4.1 | 125* | 20 min. | 0.3 | 0.3 | 10 |
| 2 | 78.3 ± 16.9 | 75 | 8 | 2.8 ± 0.6 | 2.8 | 12 |
| 3 | 78.3 ± 16.9 | 100 | 8 | 3.8 ± 0.8 | 3.8 | 43 |
| 4 | Assumed 70 | 50 | 96 | 21.6 | 5.04 | >45 |
| 5 | 74.6 ± 16.5 | 65–75 | 27** | 8.5 ± 1.9 | 7.1 | 77 |
| 6 | Assumed 70 | 75 | 96 | 32.4 | 8.1 | 11 |

Study 1 - Gaba (1990) Eur. Resour. J. 3: 450–455;
Study 2 - Present disclosure;
Study 3 - Present disclosure;
Study 4 - Haskell, et al. (1998) Invest. New Drugs 16: 81–85;
Study 5 - Agteresch, et al. (2000) Eur. J. Clin. Pharmacol. 56: 49–50;
Study 6 - Haskell, et al. (1996) Med. Pediatr. Oncol. 27: 165–173.
*ATP was infused intravenously in incremental dose levels of 0.05, 0.1, 0.15, 0.2, 0.25 μm/min/kg, each infusion lasting 20 minutes.
**ATP was infused over 30 hours. ATP infusions started at 20 μg/kg/min and increased by increments of 10 μg/kg/min every 30 minutes until the maximum dose of 75 μg/kg/min had been reached.

DETAILED DESCRIPTION OF THE INVENTION

One aspect of the present invention is a method of treating a patient having a disease associated with bone metastasis with a combination of adenosine or an adenosine analog or derivative thereof, a bisphosphonate, and a targeting PSA levels stabilized during the ATP treatment of three advanced prostate cancer patients treated with intravenously infused (i.v.) ATP (Table 2). This correlates with preclinical observations that ATP inhibits HRPA cells in vitro (Janssens and Boeynaems (2001) Br. J. Pharmacol. 132:536; Fang, et al. (1992) *J. Clin. Invest.* 89:191).

TABLE 2

| Treatment | Mean Age ± SD | n | Avg PSA before Rx, ng/ml ± SD | Avg PSA after Rx, ng/ml ± SD | PSA f % (SE) | Days post Rx to PSA measurement avg ± SD |
|---|---|---|---|---|---|---|
| Sm-153 ± TAS + Pam** | 71.8 ± 5.9 | 4 | 89.4 ± 45.8 | 86.8 ± 67.2 | −5.0 (20.4) | 24.9 ± 24.9 |
| Sm-153 + TAS | 71.6 ± 10.9 | 7 | 189.4 ± 245.8 | 225.0 ± 369.6 | 4.7 (15.3) | 33.4 ± 27.7 |
| Sm-153** | 73.9 ± 8.8 | 7 | 104.3 ± 145.4 | 219.6 ± 323.6 | 78.6 (21.3) | 45.7 ± 24.6 |
| ±TAS + Pam | 67.1 ± 9.1 | 13 | 427.0 ± 544.5 | 376.7 ± 331.6 | 1.8 (13.0) | 30.6 ± 18.0 |
| Sm-153 + TAS + Pam + ATP pretreatment | 71 | 1 | 118.6 | 19.7 | −83.4 | 28 |
| Sm-153 + TAS + Pam + ATP pretreatment | 69 | 1 | 1333 | 115.6 | −91.3 | 22 |

PSA results during treatment of advanced prostate cancer with bone metastasis (Patients followed in Radiation Oncology 1997–2002).
**P value < 0.0023

The change in PSA was expressed as a ratio rather than a strict difference due to assumed relative changes. Furthermore, assumed multiplicative error provided that the variation of PSA levels increased with an increase in PSA levels. The combination of these two assumptions provided that the PSA responses be compared on the log scale. Furthermore, it is known that the log scale stabilizes the variance (Rosner, In: Fundamentals of Bio-statistics, $5^{th}$ edition, Pacific Grove: Duxbury) and it has been observed that the variation in PSA among patients with prostate cancer is higher than in healthy (disease-free) controls.

Table 3 provides a group comparison, based on the two-sided t-test, using equal variance assumptions on the log scale. This analysis indicated that ATP pretreatment leads to a statistically significant PSA decrease following Sm-153 treatment.

TABLE 3

| Group | n | P-value |
|---|---|---|
| Sm-153 + TAS + Pam | 4 | 0.009 |
| Sm-153 + TAS | 7 | 0.003 |
| Sm-153 | 7 | 0.004 |
| TAS + Pam | 13 | 0.006 |

The t-test was defined for group comparison to ATP (i.v.) pretreatment+Sm-153+TAS+Pam (n=2). Even with the small sample size, the effect of the ATP/Pam/TAS/Sm-153 drug combination was sufficient (decrease in PSA, f %) to achieve statistically significant P-values (P-value<0.05) when compared to other treatment regimes.

Accordingly, the present invention discloses a method of treatment which combines adenosine or derivatives thereof with a bisphosphonate and a targeting agent(s) to treat diseases associated with bone metastasis.

Diseases associated with bone metastasis include cancers that spread from the primary tumor located in one part of the body to another. For example, an individual with prostate cancer may have a metastasis in their bone. Cells that metastasize are basically of the same kind as those in the original tumor, i.e.; if the cancer arose in the lung and metastasized to the bone, the cancer cells growing in the bone are lung cancer cells. Metastatic-associated diseases which may be treated by methods of the invention include, but are not limited to, skin cancer, brain cancer, ovarian cancer, breast cancer, cervical cancer, colorectal cancer, prostate cancer, liver cancer, lung cancer, stomach cancer, bone cancer, and pancreatic cancer.

The drug combination of the invention may be used for the treatment of humans or animals with cancer, including domestic, sport, laboratory, and farm animals. It is contemplated that the each component of the drug combination may be formulated into a pharmaceutical composition comprising an effective amount of the component and a pharmaceutically acceptable carrier. An effective amount of each component of the drug combination may be administered to the patient in a manner which, when combined with the other components of the drug combination, ultimately decreases the signs or symptoms of a disease associated with a bone metastasis. Examples of signs and/or symptoms that may be monitored to determine the effectiveness of the drug combination include, but are not limited to, PSA level, bone resorption, tumor size, feelings of weakness, and pain perception. Beneficial effects of the instant drug combination may, for instance, include a 50%, 75% or 100% drop in PSA levels or a reduction in tumor size by 50%, 75% or 100%. The amount of each component and the specific pharmaceutically acceptable carrier will vary depending upon, for example, the component being administered, the patient and the condition of this patient, the mode of administration, and the type of cancer being treated.

Pharmaceutically acceptable carriers are materials useful for the purpose of administering the medicament, which are preferably sterile and non-toxic, and may be solid, liquid, or gaseous materials, which are otherwise inert and medically acceptable, and are compatible with the active ingredients.

The pharmaceutical compositions may contain other active ingredients such as preservatives. The pharmaceutical compositions may take the form of a solution, emulsion, suspension, ointment, cream, granule, powder, drops, spray, tablet, capsule, sachet, lozenge, ampoule, pessary, or suppository. They may be administered by continuous or intermittent infusion, parenterally, intramuscularly, subcutaneously, intravenously, intraarterially, intrathecally, intraarticularly, transdermally, orally, bucally, as a suppository or pessary, topically, as an aerosol, spray, or drops, depending upon whether the preparation is used to treat internal or external cancers. Such administration may be accompanied by pharmacologic studies to determine the optimal dose and schedule and would be within the skill of the ordinary practitioners.

One component of the drug combination of the present method includes adenosine or a derivative thereof, also collectively referred to herein as adenosine compounds. Representative adenosine derivatives useful in the method of the invention include, but are not limited to, Adenosine triphosphate (ATP) Adenosine diphosphate (ADP); Adenosine monophosphate (AMP); AMP-PNP; $\alpha,\beta$-methylene ATP; $\beta,\gamma$-methylene ATP; or ATP$\gamma$S.

Rates of infusion of an adenosine compound may be initially administered intravenously to patients in daily dosages commencing at rates ranging from 25 to 50 µg/kg/min for up to 8 hours. Gradual increments ranging from 25 to 50 µg/kg/min up to a daily maximum of 100 µg/kg/min may be administered for eight hours to determine the maximal therapeutic efficacy and minimum toxicity.

For intravenous injection of an adenosine compound, the dose may be about 1 to 100 mg/kg of body weight. The solution may contain antioxidants, buffers, and the like. If applied topically as a liquid, ointment, or cream, the adenosine compound may be present in an amount of about 100 mg to about 500 mg of the composition. For oral administration, the adenosine compound may be administered, for example, as an enterically coated preparation or as a suspension or solution and should be administered in an amount of about 1 to 100 mg/kg of body weight per day. As one of skill in the art may appreciate, oral dose ranges of 25 to 1000 mg may be administered three or four times a day.

Rates of oral administration of an adenosine compound may be initially administered to patients in daily dosages commencing at 20 to 100 mg four times a day. Gradual increments ranging from 20 to 100 mg four times a day may be administered to determine the maximal therapeutic efficacy and minimum toxicity.

The adenosine compound may also be formulated for injection and may be presented in unit dose form in ampules or in multi-dose containers with an added preservative. The pharmaceutical composition may take such forms as suspensions, solutions, or emulsions in oily or aqueous vehicles, and may contain formulatory agents such as suspending, stabilizing and/or dispensing agents. Alternatively, the active ingredient may be in powder form for constitution with a suitable vehicle, e.g., sterile, pyrogen-free water, before use.

Alternatively, for cancers of the skin, or other external tissues, the compositions are preferably applied to the affected part of the body of the patient as a topical ointment or cream. The adenosine compounds may be presented in an ointment, for instance with a water soluble ointment base, or in a cream, for instance with an oil in water cream base, in a concentration of from about 100 mg/L to 500 mg/L.

The compounds may also be applied into body orifices such as the nose and oral cavity in the form of spray or drops. They may be applied into body orifices such as the rectum and vagina in the form of a suppository or cream.

It will be appreciated that extensive skin cancers may require the use of higher doses.

In a preferred embodiment of the present invention, an adenosine compound may further be administered in combination with agents which block adenosine receptors. Agents which inhibit adenosine receptors may be administered to a patient before, simultaneously with, or following, or before, simultaneously with and following the administration of the adenosine compound and/or the targeting agent. Exemplary inhibitors of adenosine receptors include, but are not limited to, caffeine, IB-MECA, C1-IB-MECA. Dosing will depend on the inhibitor administered and a precise pharmaceutically effective amount may be readily determined by the caregiver or clinician. Appropriate amounts may be determined by routine experimentation from animal models and human clinical studies. For example, caffeine may be administered as, for example, coffee, soft drinks, CAFFEDRINE®, QUICK-PEP®, ENERJETS®, VIVARIN®, NO-DOZ® and the like. In general, it is contemplated that five cups of coffee, consumed every 4 to 6 hours during the course of administration of adenosine compounds effectively inhibits adenosine receptors to block adenosine uptake and increase extracellular levels of adenosine compounds.

It is further contemplated that adenosine deaminase inhibitors (e.g., coformycin, 2'-deoxycoformycin) may be administered in combination with the adenosine compounds.

Another aspect of the invention provides bisphosphonates for the treatment of diseases associated with bone metastasis. Bisphosphonates may be administered to a patient before, simultaneously with, or following, or before, simultaneously with and following the administration of the adenosine compound and/or the targeting agent. Exemplary bisphosphonates which prevent bone resorption include, but are not limited to, pamidronate, alendronate, neridonate, olpadronate, ibandronate, risedronate, incadronate, clodronate, etidronate, zoledronic acid, cimadronate, piridronate, tiludronate, YH529, U-91502, PNU-91638, and EB-1053.

The precise dosage of the bisphosphonate will vary with the dosing schedule, the particular bisphosphonate chosen, the age, size, sex and condition of the patient, the nature and severity of the disease to be treated, and other relevant medical and physical factors. Thus, a precise pharmaceutically effective amount may be readily determined by the caregiver or clinician. Appropriate amounts may be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of a bisphosphonate is typically from about 1.5 to about 6000 µg/kg of body weight and preferably about 10 to about 2000 µg/kg of body weight.

For example, common human doses of alendronate which may administered are generally in the range of about 2 mg/day to about 40 mg/day, preferably about 5 mg/day to about 40 mg/day. In the U.S. presently approved dosages for alendronate are 5 mg/day for preventing osteoporosis, 10 mg/day for treating osteoporosis, and 40 mg/day for treating Paget's disease.

In alternative dosing regimens, the bisphosphonate may be administered at intervals other than daily, for example once-weekly dosing, twice-weekly dosing, biweekly dosing, and twice-monthly dosing. In such dosing regimens, appropriate multiples of the bisphosphonate dosage would be administered. For example, in a once-weekly dosing regimen, alendronate would be administered at dosages of 35 mg/week or 70 mg/week in lieu of seven consecutive daily dosages of 5 mg or 10 mg.

A further aspect of the invention provides targeting agents that may be administered to a patient simultaneously with, or following, or both simultaneously with and following the administration of the adenosine compound and/or the bisphosphonate. As used herein, a targeting agent may be a chemotherapy agent, therapeutic agent or a radionucleide used alone or in combination with other targeting agents. Similar to bisphosphonate, the dosing schedule of the targeting agent is dependent on many factors and may be readily determined by the caregiver or clinician. The targeting agents provided herein are well-known in the art and are routinely administered using standard methodologies and treatment regimes.

Chemotherapy and therapeutic targeting agents which may be used in the drug combination of the invention include, cytotoxic agents such as Taxol, Cytochalasin B, Gramicidin D, Ethidium Bromide, Emetine, Mitomycin, Etoposide, Tenoposide, Vincristine, Vinblastine, Colchicin, Doxorubicin, Daunorubicin, Mitoxantrone, Mithramycin, Actinomycin D, 1-Dehydrotestosterone, Glucocorticoids, Procaine, Tetracaine, Lidocaine, Propranolol, and Puromycin and analogs or homologs thereof. Therapeutic agents include, but are not limited to, antimetabolites (e.g., Methotrexate, 6-Mercaptopurine, 6-Thioguanine, Cytarabine, 5-Fluorouracil, Decarbazine), alkylating agents (e.g., Mechlorethamine, Thiotepa, Chlorambucil, Melphalan, Carmustine (BCNU), Lomustine (CCNU), Cyclophosphamide, Busulfan, Dibromomannitol, Streptozotocin, Mitomycin C, Cis-Dichlorodiamine Platinum (II) (DDP), Cisplatin), anthracyclines (e.g., Daunorubicin (formerly Daunomycin) and Doxorubicin), antibiotics (e.g., Dactinomycin (formerly Actinomycin), Bleomycin, Mithramycin, and Anthramycin (AMC)), anti-mitotic agents (e.g., Vincristine and Vinblastine) and new agents such as Selective Apoptotic Antineoplastic Drugs (SAANDs) such as Aptosyn® (Exisulind).

Exemplary targeting agents for the treatment of brain cancer include Procarbazine, platinum analogs (e.g., Cisplatin, Carboplatin), the Nitrosureas, BCNU, Paclitaxel, Irinotecan, Topotecan, Tamoxifen, and Temozolomide.

Targeting agents for the treatment of ovarian cancer may include one or more of the following: Etoposide, Melphalan, Cisplatin, Carboplatin, Paclitaxel, Anthracyclines (e.g., Doxorubicin), Hexamethylamine (Altretamine), Progestins (e.g., Medroxyprogesterone acetate, Megestrole acetate), 5-Fluorouracil plus Leucovorin (to counteract folic acid antagonists), Ifosfamide, or Topotecan.

Targeting agents for the treatment of breast cancer may include Doxorubicin, Paclitaxel, Methotrexate, 5-Fluorouracil, Docetaxel, Thiotepa, Cis-platin, Estrogen receptor modulators such as Tamoxifen and Toremifene, Estrogens (e.g., diethylstilbestrol), Androgens (e.g., fluoxymesterone), Gonadotropin-Releasing Hormone (GnRH), Anastrozole, Aromatase inhibitors (antineoplastics), Vinorelbine tartrate, Gemcitabine hydrochloride, Progestins (e.g., Medroxyprogesterone acetate, Megestrole acetate), Trastuzumab (HERCEPTIN®), and Cyclophosphamide.

Targeting agents for colorectal cancer treatment may include Oxaliplatin, 5-Fluorouracil, or Leucovorin.

Exemplary targeting agents for the treatment of prostate cancer may include anti-androgens (e.g., Flutamide, Nilutamide, Bicalutamide, Cyproterone, Megestrol) and the Leuteinizing Hormone-Releasing Hormone analogues (e.g., Buserelin, Goserelin, Leuprolide).

Targeting agents for liver cancer treatment may include 5-Fluorouracil, Leucovorin, Raltitrexed, Mitomycin C, and CPT-1.

Targeting agents for the treatment of lung cancer may include Paclitaxel, Carboplatin, Vinorelbine tartrate, Gemcitabine hydrochloride, Etoposide, Doxorubicin, Ifosfamide, Docetaxel, Cyclophosphamide, Methotrexate, Lomustine (CCNU), Topotecan hydrochloride, and Cisplatin.

Radiation therapy targeting agents may include external-beam radiotherapy, internal radioactive seed implants (Brachytherapy), and hemi-body radiation. Radiation therapy uses high-energy, ionizing radiation (e.g., gamma rays) to kill cancer cells. Ionizing radiation may be produced by a number of radioactive substances, such as Cobalt (Co-60), Radium (Ra-228), Palladium (Pd-103), Iodine (I-125), Radon (Rn-221), Cesium (Cs-137), Phosphorus (P-32), Gold (Au-198), Iridium (Ir-192), Boron (B-10), Actinium (Ac-225), Ruthenium (Ru-99), Samarium (Sm-153), and Yttrium (Y-90). Radiotherapy may be applied to shrink a tumor that is later removed by surgery, to relieve symptoms, or to destroy malignant cells in a tumor that cannot be removed surgically.

The drug combination of the invention may be administered in combination with agents which relieve side effects of cancer treatment. Such agents may be administered to a patient before, simultaneously with, or following, or before, simultaneously with and following the administration of the drug combination. Examples of such agents which relieve side effects of cancer treatment include, Epoetin alfa to relieve symptoms of anemia; cell-protecting agents such as amifostine; and Strontium-89 and Samarium-153 for the relief of cancer-induced bone pain.

The invention is described in greater detail by the following non-limiting examples.

EXAMPLE 1

Methods

ATP was administered to each patient once weekly for eight consecutive weeks as an 8-hour infusion at rates of 50 up to 100 µg/kg/minute; an amount determined to be well tolerated by most patients. In the first week, all patients received ATP infusions starting at 50 µg/kg/minute and was reduced to 25 µg/kg/minute in cases where 50 µg/kg/minute was not well tolerated. If the 50 µg/kg/minute was tolerated, the ATP infusion was increased to 75 µg/kg/minute in the second week. Likewise, if the 75 µg/kg/minute was tolerated, the ATP infusion was increased to 100 µg/kg/minute in the third week. This regime was maintained until the maximally tolerated dose (MTD) was reached. During infusions, all patients were monitored closely for signs and symptoms of adverse effects to ATP. If adverse effects occurred during an ATP infusion, the infusion was terminated immediately. Treatment with Sm-153, pamidronate and TAS occurred 24-hours after the 8 weeks of ATP infusion. During the combined treatment, all patients were monitored closely for signs and symptoms of adverse effects to ATP followed by Sm-153, pamidronate, and TAS.

Patients were consenting adult patients with histologically/cytologically confirmed advanced hormone-refractory prostate cancer not curable by conventional therapies that fulfilled the standard phase 1 liver, renal and Karnofsky performance eligibility requirements. The patients also had to meet one of the two following requirements. A positive bone scan and/or imaging study for bone metastasis with accompanying bone pain had to be present with rising PSA values, identified in three consecutive PSA observations, following definitive surgery and/or radiation therapy and anti-androgen hormonal therapy. PSA levels (>10 ng/ml) and a positive bone scan and bone pain at time of initial diagnosis.

Average patient age was between 50 and 85 years of age. Patients were excluded if they met the standard phase 1 respiratory and cardiac exclusion criteria.

EXAMPLE 2

Interventions

ATP infusion therapy was as described above. ATP infusions were administered between 25 and 100 µg/kg/minute for 8 hours for 8 consecutive weeks (Table 4).

TABLE 4

| Week of Treatment | Day of Week | ATP i.v. Administration (µg/kg/min) | Sm-153 (mCi/kg/iv) | Pamidronate (mg) |
|---|---|---|---|---|
| 1 | Day 1 | 25–50 | | |
| 2 | Day 1 | 50–75 | | |
| 3 | Day 1 | 75–100 | | |
| 4 | Day 1 | 75–100 | | |
| 5 | Day 1 | 75–100 | | |
| 6 | Day 1 | 75–100 | | |
| 7 | Day 1 | 75–100 | | |
| 8 | Day 1 | 75–100 | | |
| 8 | Day 2 | | | 90, Monthly for 12 months |
| 9 | Day 1 | | 1.0 | |

Ninety milligrams of pamidronate (AREDIA®, Novartis Corporation, New York, N.Y.) was administered as a two-hour intravenous infusion monthly for 12 cycles starting from week 8, day 2.

Post-ATP treatment, anti-androgen therapy was administered to patients such that they received total androgen suppression (TAS) using a combination of a goserelin acetate implant (ZOLADEX®, AstraZeneca Pharmaceuticals LP, Wilmington, Del.) and bicalutamide (CASODEX®, AstraZeneca Pharmaceuticals LP, Wilmington, Del.). Bicalutamide, administered orally daily for the duration of goserelin acetate treatment, began on the day the first goserelin acetate depot injection (3 months) was administered.

Sm-153, (QUADRAMET®, Berlex Laboratories, Inc., Montville, N.J.) was administered as the chelate with a tetraphosphonate chelator, ethylenediaminetetramethylenephosphonic acid (EDTMP). 1.0 mCi/kg was i.v. administered on week 9 day 1.

EXAMPLE 3

Measurements

Blood samples were taken from each patient before, and at intervals during and after infusions on weeks 1, 3, and 8. ATP levels were determined in the plasma and erythrocytes of these samples using standard methodologies and were monitored was used for analysis of treatment regime. Furthermore, ATP blood parameters were measured immediately after Sm-153 treatment.

EXAMPLE 4

Statistics

The primary analysis was the measurement of blood PSA levels after Sm-153 treatment preceded by ATP infusion. The mean difference of PSA in patients treated with Sm-153 but no ATP pretreatment versus patients treated with Sm-153 and ATP pretreatment was 46.7%. Two-sided paired t-test with 7 degrees of freedom yielded the p-value less than 0.041, thus the difference of PSA percentage statistically significant for patients with and without ATP infusion across patients. Top detect this difference, the sample size calculation used assumed that the minimum detectable difference was 0.1 with standard deviation 0.2.

EXAMPLE 5

Patient 1—i.v. ATP Without Sm-153

Patient 1 was a 76-year old retired architect with hormone-refractory prostate cancer. He received the eight weekly outpatient infusions of i.v. ATP. During the course of the treatment he experience minor side effects of the ATP infusion, described as the occasional need to take a deep breath. These minor side effects did not prevent him from receiving the infusions as scheduled. At the start of the trial, his hematocrit was 33% and reached a NADIR of 25% at which point he received a transfusion. By the eighth week, at the highest dose of 100 µg/kg/min×8 hours, the patient noted improved energy levels at home and improved exercise and activity according to both the patient and his spouse. At the start of the trial, his PSA level was 2732 ng/ml. During the ATP treatments, his rate of PSA level increase stabilized. At the completion of the ATP treatments, the rate of increase of PSA levels resumed to that of rates prior to the study. The patient continued to have bone pain at the end of the eight weeks of ATP therapy and a bone scan the completion was interpreted as a super-scan. For financial and social reasons, the patient did not receive Sm-153 to palliate his bone pain.

EXAMPLE 6

Patient 2—i.v. ATP Followed by Sm-153, Bisphosphonate, and External Beam Radiation Therapy Patient 2 was a 69-year old retired general contractor with hormone-refractory prostate cancer and extensive bone metastases. PSA levels for this patient were 369 ng/ml. He received eight weeks of outpatient i.v. ATP infusions. During the weeks following completion of the ATP infusions, the PSA values began to rise with an accompanying increase in bone pain. The patient began palmidronate (bisphosphonate) treatment and was referred for radiation therapy. He initially received external beam to the painful sacroiliac joints one week after his ATP treatments concluded and was treated with a single fraction of external radiation of 800 cGy. The PSA level peaked at 1333 ng/ml one week after his ATP treatments concluded. Two weeks later, the patient received Sm-153 treatment. Approximately 3 weeks after the Sm-153 treatment, he received an additional single 800 cGy fraction external beam treatment to residual painful lumbar lesions in the lumbar vertebra. Following the Sm-153 treatment, the PSA levels exhibited an exponential decline with a $T(\frac{1}{2})$ =9.1 days.

The critical parameters for patient 2 are as follows. Time from end of ATP therapy to initial external beam radiation administration (as single fraction) was 7 days. Time from end of ATP therapy to PSA levels at a relative maximum (1333 ng/ml) was 7 days. Time from end of ATP therapy to PSA levels at a relative minimum (115.6 ng/ml) was 38 days which was a 91.3% decrease from the maximum PSA levels. Time from end of ATP therapy to Sm-153 administration was 22 days. Time from end of ATP therapy to second external beam treatment administration (as single fraction) was 44 days.

EXAMPLE 7

Patient 3—i.v. ATP Followed by Sm-153, Bisphosphonate, and External Beam Radiation Therapy Patient 3 was a 72-year old retired railroad conductor with hormone-refractory prostate cancer. He was diagnosed with prostate cancer and initially responded to TAS. One year later he underwent a left nephrectomy for renal cell cancer. In the following year, his PSA levels steadily rose despite anti-androgen hormonal therapy, indicative of the hormone-refractory prostate cancer. He began receiving i.v. ATP the following year and because of increasing bone pain, particularly in his hip and pelvis, he only received four courses of the i.v. ATP. This included two courses of the highest dose-rate (100 μg/kg/min). After his last ATP infusion, he was referred for radiation treatment. He received external beam radiation to his hip and pelvis and was also administered Sm-153. He received 3000 cGy in 10 fractions beginning nine days after his last ATP treatment and ending two weeks later. He was administered Sm-153 infusion on the second day of his external beam radiation treatment; 10 days after his last ATP treatment. His peak PSA level (118.6 ng/ml) was measured on the same day as his Sm-153 treatment. Subsequent PSA levels exhibited an initial exponential decline with a T(½)=10.1 days. This rate of PSA decrease continued for six weeks when the PSA level reached 5.74 ng/ml. The following week the PSA level reached undetectable levels. The patient's spirits improved dramatically and he noted that he was no longer aware of having prostate cancer.

The critical parameters for patient 2 are as follows. Time from end of ATP therapy to initial external beam radiation was 9 days. Time from end of ATP therapy to PSA levels at a relative maximum (118.6 ng/ml) was 10 days. Time from end of ATP therapy to PSA levels at a relative minimum (0.0 ng/ml, NADIR) was 55 days which was a 100% decrease from the maximum PSA levels. Time from end of ATP therapy to Sm-153 administration was 10 days.

EXAMPLE 8

Patient 4—Sm-153 and External Beam Radiation Therapy Without ATP

Patient 4 was a 82-year old retired contractor with hormone-refractory prostate cancer. Because of a positive bone scan and severe bone pain in the pelvis and lower back, he was referred to Radiation Oncology for ATP administration and radiation therapy. He was administered Sm-153 and external beam radiation. PSA levels exhibited no PSA NADIR but rather increased during and following the therapy. The patient did, however, have some palliation of the pain.

EXAMPLE 9

Patient 5—Oral ATP Followed by Bisphosphonate and Sm-153

Patient 5 received three weeks of oral ATP at a dose of 30 mg by mouth four times a day followed by intravenous zoledronic acid (ZOMETA®, 4 mg). Subsequently, the patient received 1 mCi/kg of Sm-153 treatment. The patient tolerated all the therapies well and a post-treatment Prostascint scan revealed an absence of the bone-metastases that had been evident on a pre-treatment Tc-99 bone scan. Evident was an abdominal lesion and residual disease in the prostatic bed. The patient will receive localized external beam radiation therapy to the non-osseous lesions.

What is claimed is:

1. A method of treating prostste cancer associated with bone metastasis comprising administering to a patient with prostate cancer associated with bone metastasis an effective amount of adenosine triphosphate in combination with a bisphosphonate and at least one targeting agent to decrease the signs and symptoms of prostate cancer, wherein said bisphosphonate is pamidronate and said targeting agent is samarium-153.

2. A method of treating prostate cancer associated with bone metastasis comprising administering to a patient with prostate cancer associated with bone metastasis an effective amount of adenosine triphosphate in combination with a bisphosphonate, at least one targeting agent, and an agent which blocks adenosine receptors to decrease the signs and symptoms of prostate cancer, wherein said bisphosphonate is pamidronate and said targeting agent is samarium-153.

* * * * *